United States Patent [19]

Gaukroger

[11] Patent Number: 5,077,767

[45] Date of Patent: Dec. 31, 1991

[54] DETERMINING THE EXISTENCE OF MISORIENTATION IN A CRYSTAL

[75] Inventor: Michael P. Gaukroger, Fleet, England

[73] Assignee: Gersan Establishment, Vaduz, Liechtenstein

[21] Appl. No.: 613,917

[22] PCT Filed: Jun. 14, 1989

[86] PCT No.: PCT/GB89/00664

§ 371 Date: Feb. 14, 1991

§ 102(e) Date: Feb. 14, 1991

[87] PCT Pub. No.: WO89/12816

PCT Pub. Date: Dec. 28, 1989

[30] Foreign Application Priority Data

Jun. 16, 1988 [GB] United Kingdom ............... 8814343

[51] Int. Cl.$^5$ ............................................. G01N 23/20
[52] U.S. Cl. ......................................... 378/73; 378/74; 378/71
[58] Field of Search ................ 378/70, 73, 74, 76, 378/79, 80, 82, 86, 87, 44, 51, 58, 71, 72

[56] References Cited

U.S. PATENT DOCUMENTS 3,833,810  9/1974  Efaneu et al. ..................... 375/74
4,125,770  11/1978  Lang .
4,217,493  8/1980  Li et al. .

FOREIGN PATENT DOCUMENTS 1553822  10/1979  United Kingdom .

OTHER PUBLICATIONS

Berger, H., *A Simple X-Ray Topographic Technique for Studying the Coarse Perfections of Crystals*, Kristall und Technik, 1977.

Orlov et al., "A study of the Internal Structure of Variety III Diamonds by X-ray Section Topography", *Phys Chem Minerals*, 1982, pp. 105–111.

"Using Synchrotron X-Radiation Topgraphy", J. Appl. Physics, Jul. 1987, pp. 137–144.

Aristov et al., "A Study of the Imperfections and Crystallographic Characteristics of Crystals by Scanning in a Widely Divergent X-Ray Beam", Sov. Phys. Crystallogr., 3–4, 1976, pp. 191–195.

*Primary Examiner*—Edward P. Westin
*Assistant Examiner*—David P. Porta
*Attorney, Agent, or Firm*—Kerkam, Stowell, Kondracki & Clark

[57] ABSTRACT

A method and apparatus for determining the existence of misorientation in a crystal, comprising irradiating the crystal with X-rays pre-orientating any crystallographic plane of the crystal with respect to the axis of the X-rays, imaging X-rays received from the crystal so as to cause a plurality of effectively angularly-separated images to be formed, the energy of the X-rays being such that while carrying out the method at least some of the X-rays forming the images have intersected the whole depth of the portion of the crystal being examined, and determining the existence of any misorientation from the images.

18 Claims, 10 Drawing Sheets

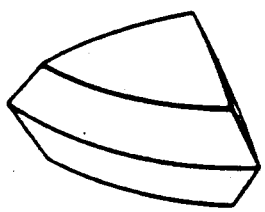
FIG. IA
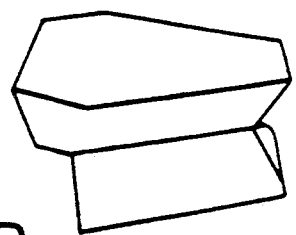
FIG. IB
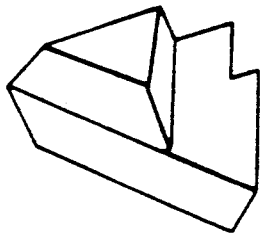
FIG. IC
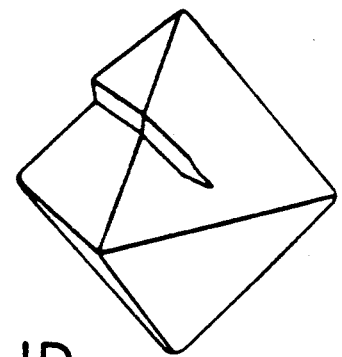
FIG. ID
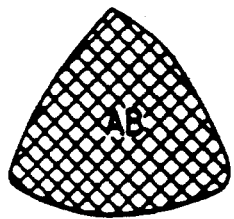
FIG. 2A
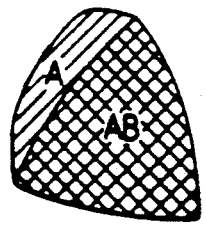
FIG. 2B
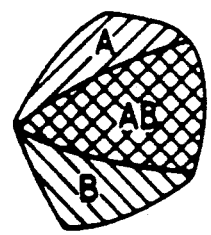
FIG. 2C

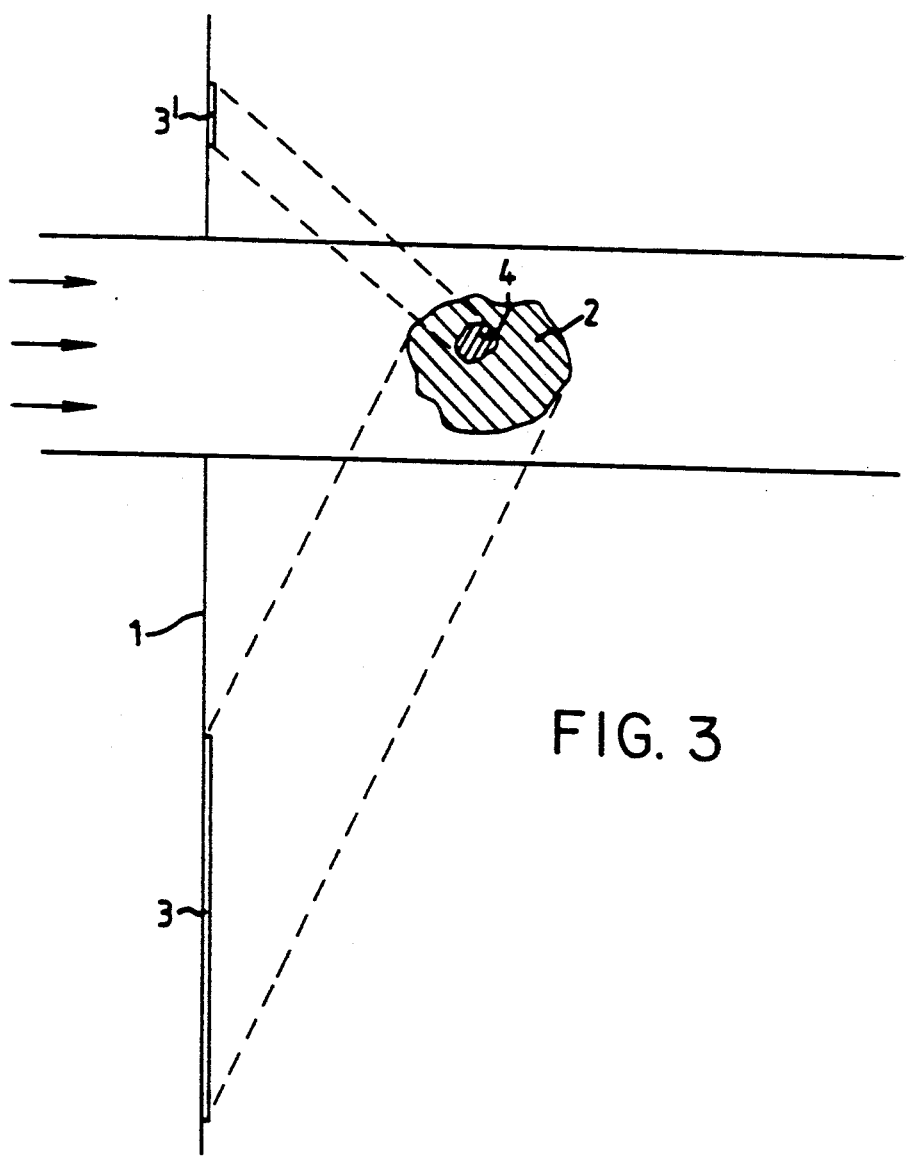
FIG. 3
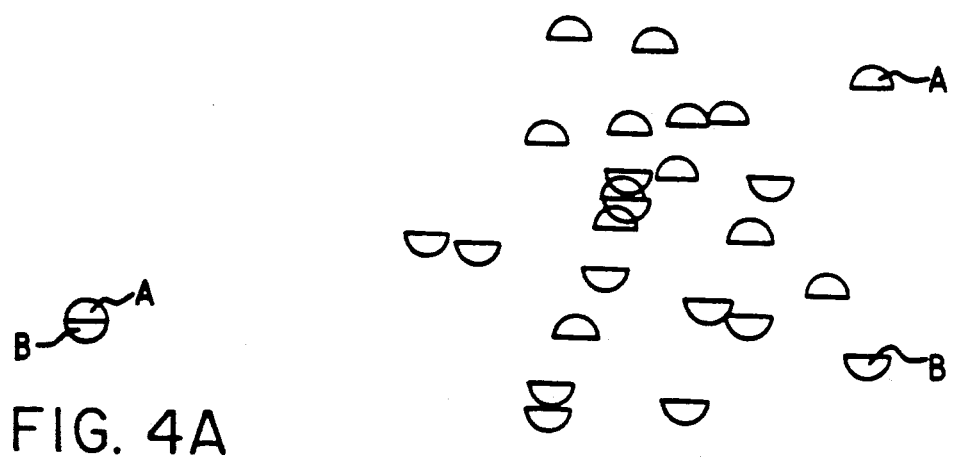
FIG. 4A
FIG. 4B

FIG. IIA

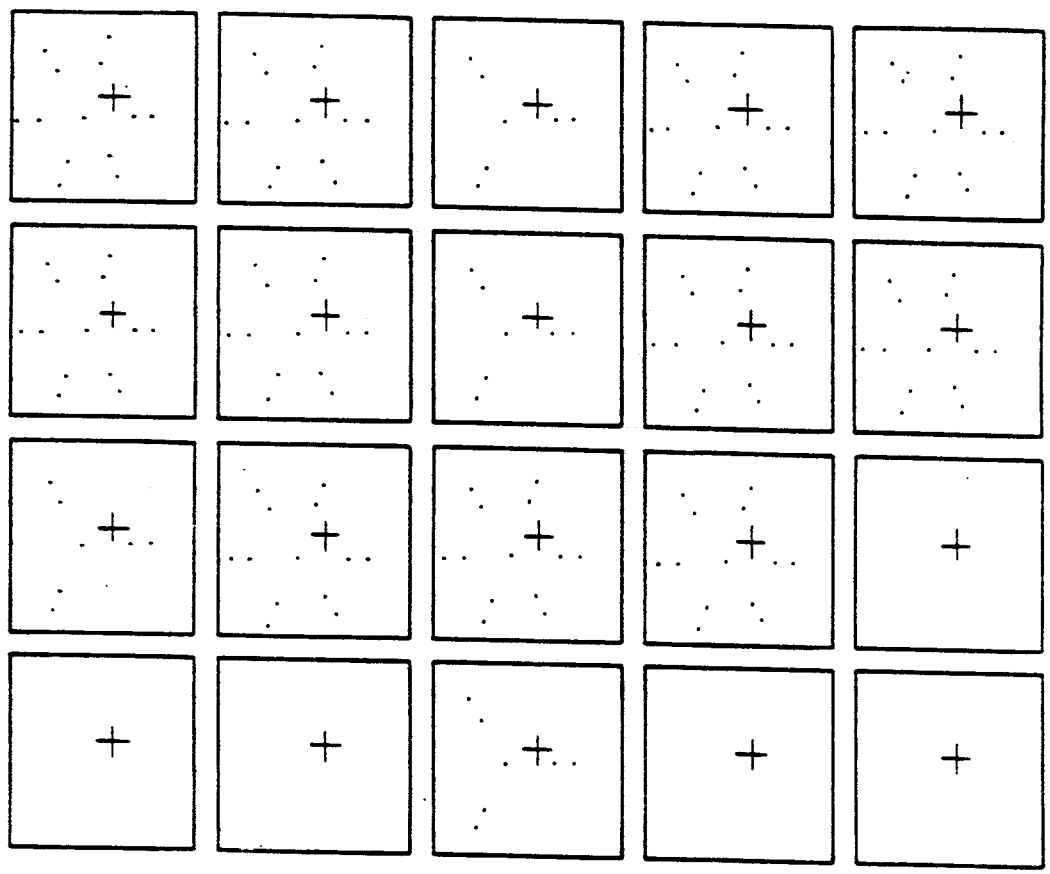
FIG. 11B
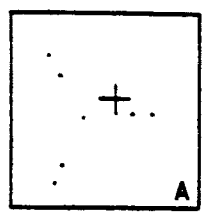
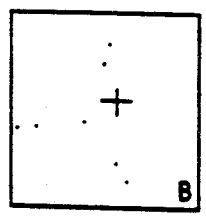
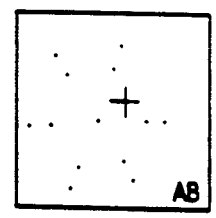
FIG. 11C

DETERMINING THE EXISTENCE OF MISORIENTATION IN A CRYSTAL

BACKGROUND OF THE INFORMATION

This invention relates generally to determining the existence of misorientation in a crystal (this includes determining the non-existence of misorientation). Though the invention has general applicability, it is particularly applicable to gemstones, especially diamonds; without limiting the scope of this invention, the remainder of this specification relates to diamonds.

Various stones give problems in the diamond industry, amongst which can be listed polycrystals, bicrystals, twinned crystals, strained crystals, crystals with inclusions, cracked stones, coateds, and crystals with growth bands.

The present invention is primarily concerned with polycrystals (a bicrystal is a special case of a polycrystal) and twinned crystals. In each case, there is misorientation—one or more volumes of the crystal have a different crystallographic orientation to the remainder. A polycrystal grew from more than one seed or nucleus and there is no crystallographic orientation relationship between the differently orientated volumes. During the growth of a twinned crystal, the orientation changed; although one or more volumes have a different orientation, there is an orientation relationship. A twinned crystal is considered to be a type of single crystal. The formation of a maccle is the type of twinning that occurs in diamonds. A maccle is a form of twinned crystal in which the lattice of one part of the stone is apparently rotated 180 degrees about the [III] direction to form a twin boundary on the (III) plane. Physical rotation does not actually occur—the twinning occurs during growth. FIGS. 1a to 1d of the accompanying drawings shows stone shapes resulting from the maccle transformation.

In this specification, the terminology is as explained above, which is the crystallographic terminology. In the diamond industry, bicrystals are called twins.

The existence of two different orientations within a stone can cause problems during manufacture. In many cases, the only option is to manufacture solely by polishing, i.e. the stone cannot be sawn or cleaved using conventional procedures.

Polycrystals and twinned crystals (and particularly twinned crystals) are probably the most difficult stones for inexperienced sorters to master because of the many types and the different techniques used in their identification. Stone shape often indicates a stone might be a polycrystal or twinned but manual classification is only complete when a line at the boundary between misoriented regions of the crystal has been identified. In nearly all cases, the boundary extends to the surface of the stone.

In order to distinguish between a polycrystal or twinned crystals and a non-twinned single crystal, a sorter often needs to look into the bulk of the stone. Knowledge of refraction effects at the stone surface helps the sorter work out the position of internal features. Experience helps the sorter to distinguish between a line indicating misorientation and trails (i.e. growth pattern) on the surface of a stone. It would be very difficult to build a machine which sorted polycrystals or twinned crystals using even the external features because of the variety of ways that a polycrystal or twinned crystal is identified. It is unlikely that optical image processing could allow a machine to distinguish between e.g. a herringbone maccle line and normal trails.

A technique which gives bulk orientational information or contrast would have the advantage that an orientation difference is common to all polycrystals and twinned crystals. However, unless flats were polished on each stone, any optical technique which involved using internal information would require the refractive index of the stone and surrounding medium to be matched. Immersion in a matched refractive index liquid would present engineering problems. Also, all known liquids having refractive indices approaching that of diamond (2.4) are toxic. In addition, it may be desirable to make a distinction between polycrystals and twinned crystals to prevent polycrystals being sorted as twinned crystals.

GB 1 547 371 discloses an X-ray technique for identifying specific diamonds, where a record is made of a diamond using an X-ray beam which is carefully oriented in relation to the crystallographic orientation of the diamond, to produce an X-ray topograph; the diamond can be recognised again even if it has been re-cut, because it will produce a similar topograph.

GB-A-2 107 560 discloses the use of a Laue diffraction pattern as a manufacturing control to ensure that the orientation of a single crystal turbine blade is such that a crystallographic plane is parallel to a planar prepared surface, the equipment being carefully oriented relative to the prepared surface.

THE INVENTION

According to the invention, X-ray imaging is used without pre-orientating the crystal.

The imaging is made by Laue photography, but it is not necessary that a permanent image be made. The images produced by Laue photography are termed Laue spots, and each Laue spot is produced by a transmitted or reflected diffraction beam by all those lattice planes for which the Bragg condition is fulfilled, the X-ray beam usually containing X-radiation of different wave lengths. There is a good description of the Laue method in "Elements of X-Ray Diffraction", 2nd Edition, by Cullity, from page 92.

Using the invention, one can distinguish between non-twinned single crystals and twinned crystals or polycrystals. Not only the presence but also the position of twinning (i.e. the boundaries, which are also termed composition planes) can be estimated or even precisely located. There is no need to pre-orientate the sample, i.e. to pre-orient any crystallographic plane of the crystal with respect to the axis of the X-rays; nonetheless at some orientations of the stone, the position of the misorientation could be hard to detect, e.g. if the boundary is normal to the axis of the X-ray beam. There is no need to polish a planar surface on the sample or to remove surface defects in general—the surface need not be optically clear.

According to a first technique, the presence of a twinned crystal or polycrystal can be detected by counting the number of spots within a certain area, say within a cone having a certain half-angle. The incident beam should be such that it intersects both orientations (if two are present) while carrying out the method. With a twinned crystal, some Laue spots appear to be produced from the whole crystal (rather than from a part of it) because some planes of atoms are common to both crystal orientations; specifically the (111) plane would be common to both parts of the stone. If there is no orientational relationship between the two crystals, i.e. in polycrystals, the total number of spots is, on average, double the number of spots (compared to a single crystal) because the two orientations are largely independent. Though it is not easy to distinguish a twinned crystal from a polycrystal, this is not important as it is usually possible to distinguish them using a shape sort, which can be automated. Large, single crystal inclusions could be detected.

As the incident beam must intersect both orientations for two patterns to show, and as the incident beam must intersect the total volume of the stone while carrying out the method, for the technique to be reliable, this places a lower limit on the energy of X-radiation, it being the energy which determines the penetration depth. There are known curves which indicate the thickness of a diamond which will be penetrated before the relative intensity falls to a predetermined value, and the required energy can be calculated, e.g. for the deepest stone that would be examined. However, it is only necessary that some of the X-rays should intersect the full depth of the portion of the crystal being examined, during the course of carrying out the method. For instance, with a crystal such as diamond with a symmetrical lattice, one half can be examined and then the crystal be rotated through 180° to turn it over, the other half then being examined. Thus in effect the X-rays need only penetrate half-way through the crystal, though this is not preferred.

Once the position of the misorientation has been detected, Laue photographs of a volume having a single orientation, whether of transmitted or back-reflected rays, could if desired be used to find the orientation in that volume, particularly with diamond since diamond has a cubic lattice. However, normal diamond polishing techniques do not require the actual orientations to be known.

Primarily, the invention is useful for sorting (which includes physical separation or just classifying without separating the categories). Sorting accuracy can be improved by introducing a further sorting category to re-sort stones for which the number of Laue spots (or any chosen parameter) falls within a boundary or overlap zone; such re-sort stones could be examined when presenting another orientation to the X-ray beam, or merely returned to the feeding system for re-sorting on a random basis.

The invention can be carried out using a broad beam (X-ray beam is large enough to irradiate the whole crystal) or using a narrow beam (the X-ray beam is not large enough to irradiate the whole crystal), normally the whole crystal being scanned in the latter case. Preferably the beam in each case is nominally parallel.

Thus the whole of a small sample may be irradiated if the beam is larger than the sample—typically, the maximum sample size for this would be 6 mm. The cross-section or diameter of the beam can be arranged so that the beam would contain the largest stone being examined. The Laue spots are then the same size and shape as the projected area of the volume giving rise to the diffraction which form the spot region—each Laue spot becomes a sort of low resolution diffraction topograph of the stone. The main difference is that most Laue spots are produced by reflection of the background radiation, whereas topographs use reflection of the characteristic radiation to provide contrast arising from orientation changes and small changes in lattice parameter. The broad beam technique can yield information regarding the size of the stone and the size and position of any misorientated regions, which however is difficult to interpret manually or automatically.

In the alternative, a narrow beam can be used; preferably the stone is moved in the incident beam, although the beam can be moved over the stone. Scanning rates are relatively slow, which is a disadvantage. However, scanning is a most practical way of examining larger stones. An advantage of using a narrow beam is that the narrower beam gives greater spatial resolution. With scanning, a second, different technique may be employed in which the images are viewed periodically in order to determine if the Laue pattern has changed, using picture differencing; a change indicates that the sample is not crystallographically homogeneous and indicates where the change in crystal orientation takes place. Thus this technique can be used to accurately indicate where the misorientated volume or volumes are, the accuracy being greater than using a broad beam.

Other techniques are possible, such as looking at the range of areas or lengths of circumferences of the spots and determining the peaks in their distribution, each peak representing a volume of a different orientation, or using convex hole deviance (deviance from the closest convex shape drawn around the spot).

Information as to the size and shape of the differently orientated volumes can be obtained by determining the ratio of the number of images, or their total area, from each volume.

Nearly real-time imaging can be achieved, for example using either an X-ray sensitive camera or a phosphor plate and a low-light-level camera. An image intensifier tube can be incorporated to reduce the X-ray flux required to produce an image. Actual real-time is not preferred because some processing such as integration is necessary to reduce noise to a reasonable level—bloom can be removed by shading correction using available dedicated hardware. Image processing and analysis can be done automatically by a computer in order to distinguish between various types of stone.

The invention can be carried out using back-reflection (back-scatter) or transmission. In transmission, the longest path of X-rays passing through the stone is reduced in length, compared with back reflection. However, the transmitted beam and additional scatter was found to render more of the film unusable (when using film), though a transmitted beam enabled shorter wave length X-rays to be used, thereby reducing exposure times. Detector developments may enable transmitted radiation to be detected on the axis of the source, or symmetrically around the axis.

A symmetrical pattern of images need not be produced. The symmetry or otherwise depends upon the geometry of the X-ray source, crystal and detector, and also upon the orientation of the crystal. The source-crystal-detector geometry is preferably that which gives the smallest spread in the number of Laue spots when crystals are randomly orientated; fewer additional spots need be detected to classify the crystal correctly, having regard to the overlap of single crystal and twinned crystal spot distributions. The physical size of the detector and its proximity to the X-ray beam can be a limiting factor. However, the preferred geometry is believed to be reflection at 90°.

The X-rays can be polychromatic or white, or can be monochromatic—monochromatic X-rays are not preferred as fewer Laue spots are apparent. Minimum energy (maximum wavelength) X-rays are preferred, particularly for reflected images, as they allow images to be detected for the longest path lengths through the crystal.

The crystal examined need not form the complete article—i.e. the invention can be used to examine just part of a stone.

The images need only be effectively angularly-separated and not actually angularly separated. Thus using electronic detection at a single location, the crystal could be rotated. Also, in general terms, the crystal can be rotated e.g. on a goniometer, though this is not preferred.

THE DRAWINGS

FIGS. 1a to 1d are views of four typical twinned crystal (maccle) shapes;

FIGS. 2a to 2c illustrate the criterion for identifying a crystal with two orientations;

FIG. 3 illustrates a broad beam method of the invention, in a schematic manner;

FIG. 4a illustrates a classical diamond maccle;

FIG. 4b shows the images produced when examining the maccle of FIG. 4a, using the method of FIG. 3;

FIG. 11a shows grid positions on a diamond;

FIG. 11b is a sketch of a grid of photographs showing images produced by the method of FIG. 9 at the positions shown in FIG. 11a; and FIG. 11c shows the three different patterns visible in FIG. 11b.

FIGS. 1a TO 1d

These Figures show classical diamond maccles, FIGS. 1a and 1b showing triangular shapes, FIG. 1c showing a step shape and FIG. 1d showing an octahedron shape;

FIGS. 2a, 2b and 2c

For good discrimination, particularly when scanning, there must be somewhere where there is a full thickness of the crystal which has only one orientation. FIGS. 2a to 2c shows three maccles having parts A, B of different orientation. The FIG. 2a maccle is not easily detectable whereas the FIG. 2b and FIG. 2c maccles are easily detectable.

FIG. 3

FIG. 3 shows the formation of a Laue spot using a broad (though collimated) beam which is passed through the central opening in a film or detector 1 so that the whole crystal 2 is irradiated simultaneously. Laue spots 3, 3' are formed (only two are shown). The size of the Laue spot 3' is a measure of the size of the volume 4 which has a different orientation.

FIGS. 4a and 4b

The parts A, B of different orientations in a maccle are shown in FIG. 4a, and FIG. 4b in a Laue photograph taken using the method of FIG. 3. In FIG. 4b, the spots A, B come from the parts A, B, respectively. Each spot is a kind of diffraction topograph. If the misorientated region is thick, the spot is more intense (the intensity of the diffracted beam is proportional to the volume of the diffracting material).

Figure 5A:
FIGS. 5a and 5b are photographs showing images produced from a non-maccled single crystal and a maccle, respectively, using the method of FIG. 3.
Figure 5B:

FIGS. 5a and 5b

FIGS. 5a and 5b are reproductions of actual prints using a broad beam with the arrangement of FIG. 3. FIG. 5a shows a non-maccled single crystal, i.e. with all the orientation the same, whereas FIG. 5b shows a maccle. In the print of FIG. 5b, there are many more Laue spots. As indicated above, the size and shape of each Laue spot is an indication of the size of the region producing it, and FIG. 5b shows that the sample corresponds to that shown in FIG. 4a, i.e. the crystal is half one orientation and half the other (which is common with maccles). It can be seen that nearly every image in FIG. 5b is a mirror image of another image, and the surface where the two images would join represents the boundary between the volumes of different orientation. It is apparent, particularly in FIG. 5b, that the intensity of the spots is less at the edges due to the rounding off of the crystal and thus the presence of less material. In FIG. 5a, the triangular spots represent the projected shape of the stone. In FIG. 5b, the stone was more eliptical in projected shape.

FIG. 6

Figure 6:
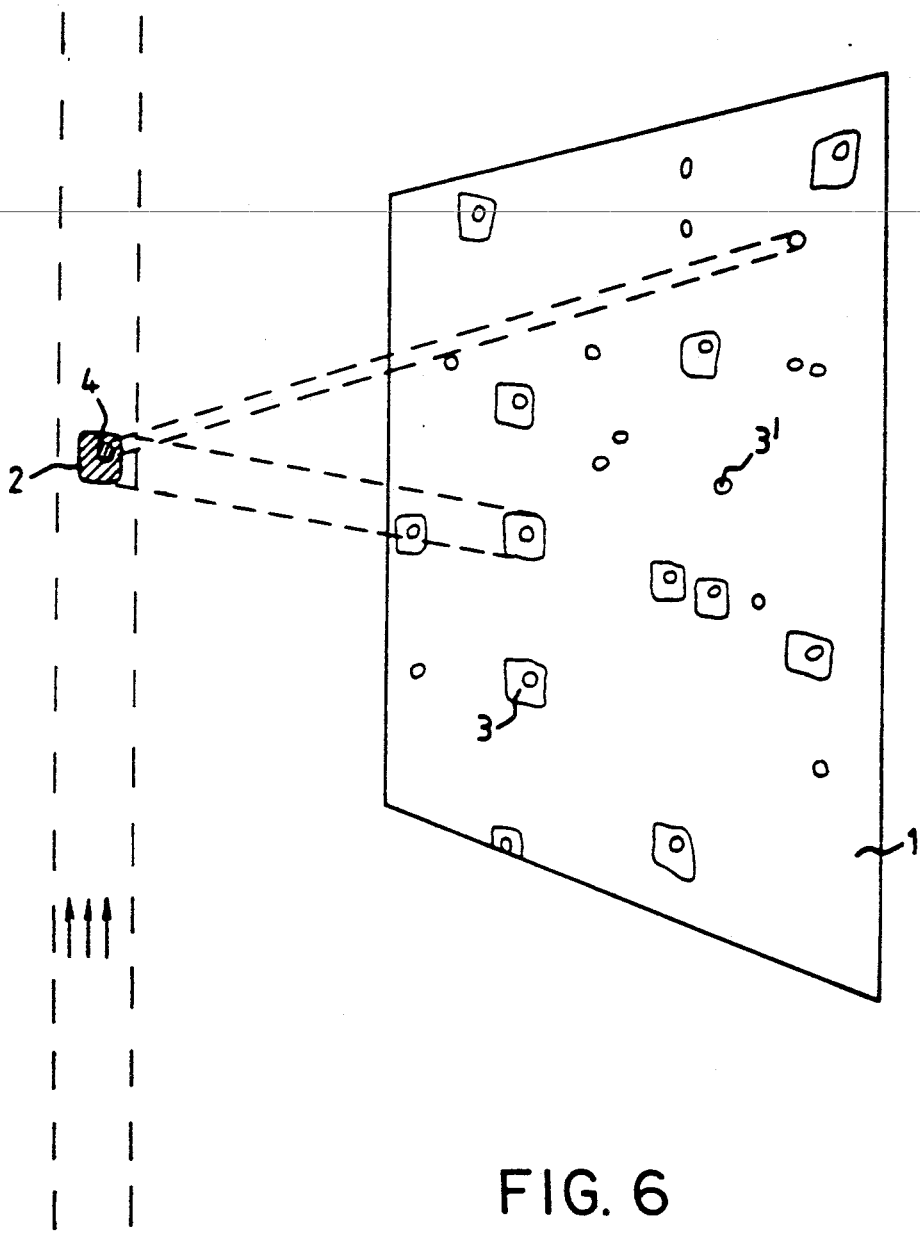
FIG. 6 illustrates another broad beam method of the invention, in a schematic manner.

FIG. 6 shows the formation of Laue spot using a broad beam and detecting the reflected images nominally at 90° (source-crystal-detector angle). Here the crystal 2 is shown as blocky form with a small volume 4 of misorientation. The Laue spot 3 formed by the main volume of the crystal 2 have a non-exposed patch corresponding to the misorientated volume 4, there being further Laue spots 3—corresponding the misorientated volume 4. The extent of the misorientated volume 4 can be determined by notional back projection of the Laue spot 3, 3' to the crystal 2.

Figure 7A:
FIGS. 7a to 7d are photographs showing images produced by the method of FIG. 6 from a non-maccled single crystal, an equal volume maccle, a bicrystal with a small misorientated region, and a different view of the same bicrystal, respectively.
Figure 7B:
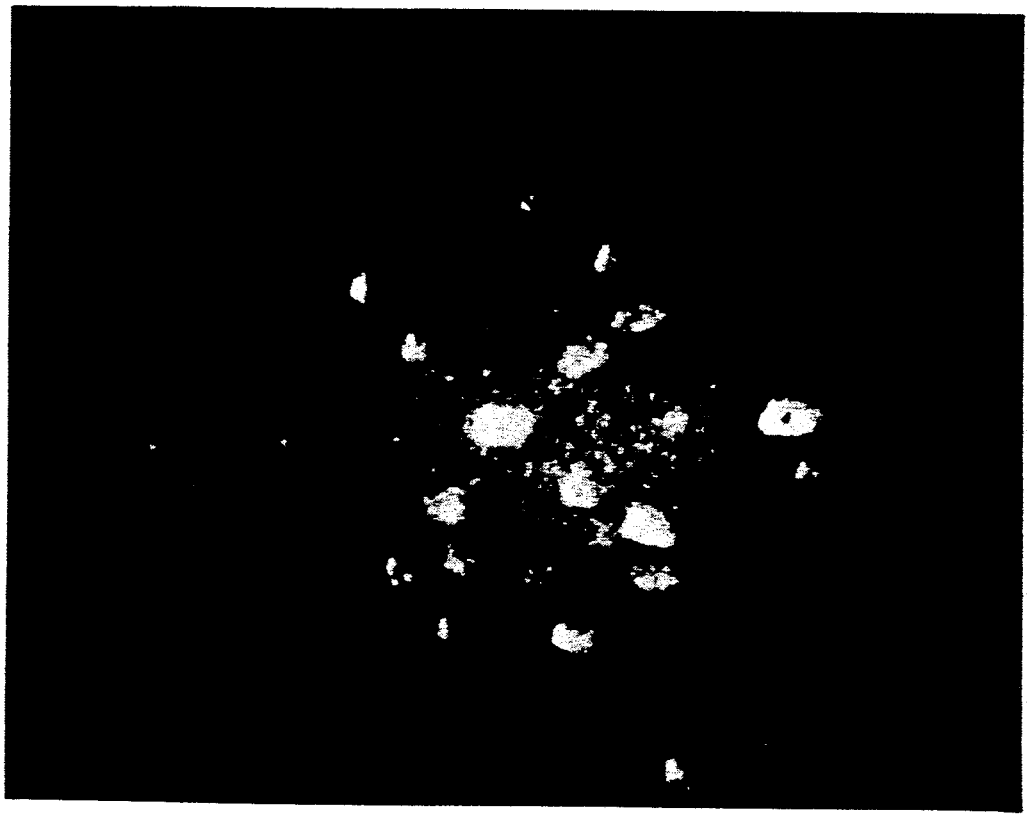

FIGS. 7a to 7b

FIG. 7a shows the Laue spots from a single non-maccled crystal. The section of the crystal giving rise to the spots is equal in shape to the back-projection of the spot. It will be seen that the crystal is a blocky crystal.

FIG. 7b is a photograph of Laue spots from a maccle. It will be seen that there are many more spots than in FIG. 7a, approximately double, which indicates that the crystal is a maccle.

Figure 7C:
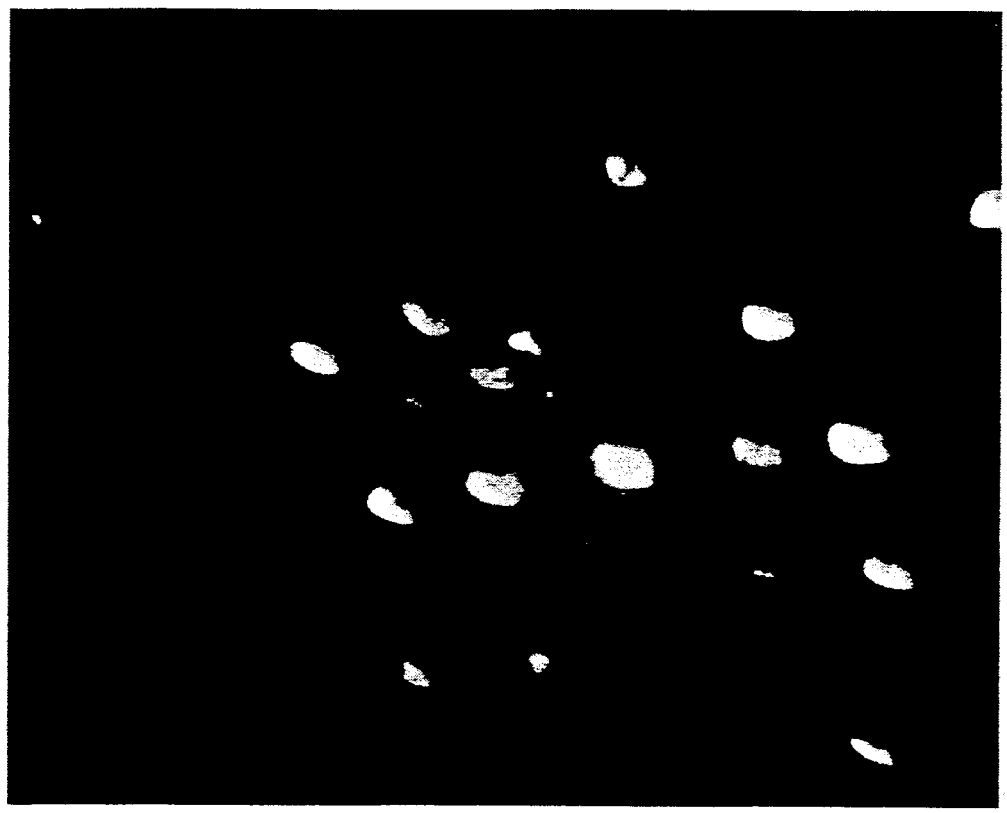
Figure 7D:
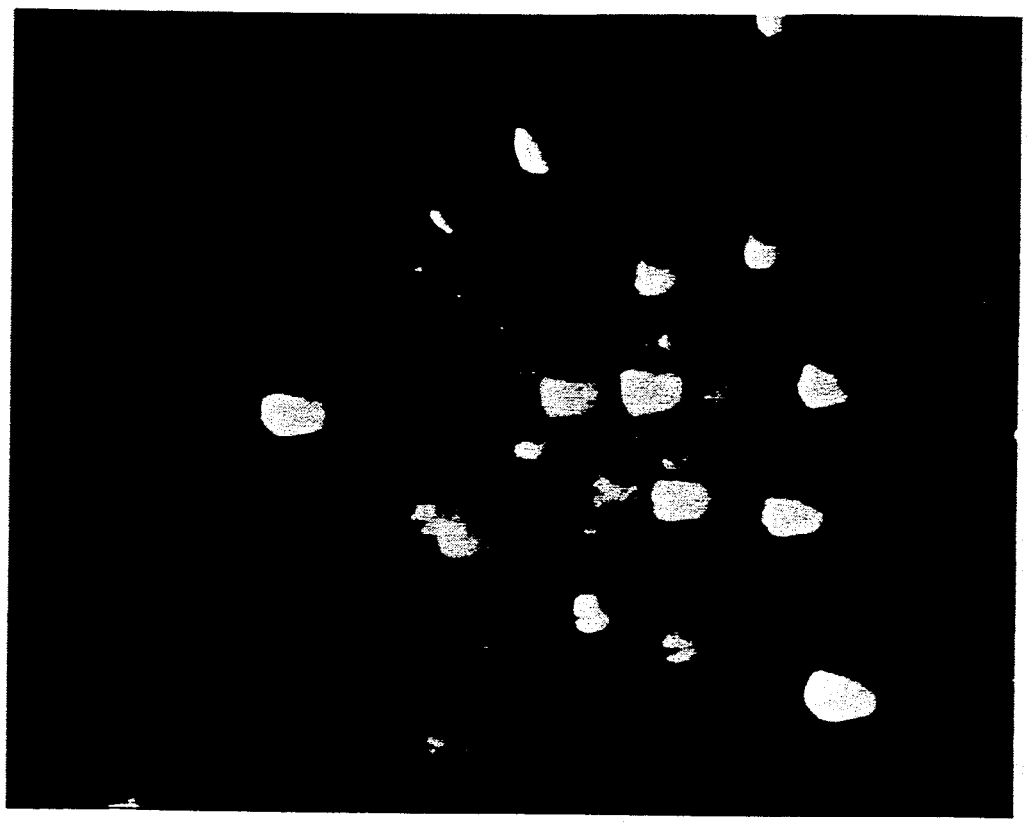

FIGS. 7c and 7d are of the same crystal, but the crystal is in different orientations. The crystal has a small misorientated volume. In the larger spots, which are projections of the whole crystal section, the small misorientated volume can be seen as a non-exposed, elongate patch; the smaller spots are projections of the misorientated volume, and they are elongate.

Figure 8A:
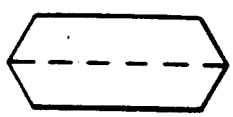
FIG. 8a illustrates another equal volume maccle and FIG. 8b shows the images produced when examining the maccle using the method of FIG. 3 or FIG. 6.
Figure 8B:
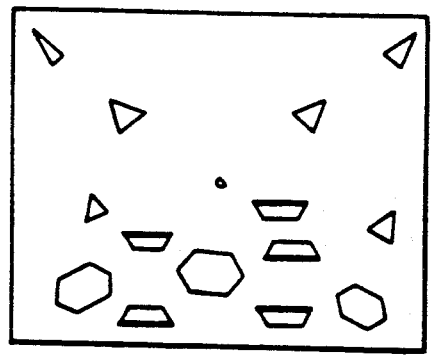

FIGS. 8a and 8b

FIG. 8a represents a section through a typical maccle shape, similar to that of FIG. 1a, the boundary between the two orientations being shown in dashed lines. FIG. 8b represents the images produced by the method of FIGS. 3 or 6. It will be seen that some of the images are mirror images of other images, and these images have been marked to show the boundary (composition) plane with a thicker line. The complete spots are all derived from planes which are normal to the composition plane and are common to both orientations in the maccle.

FIG. 9

Figure 9:
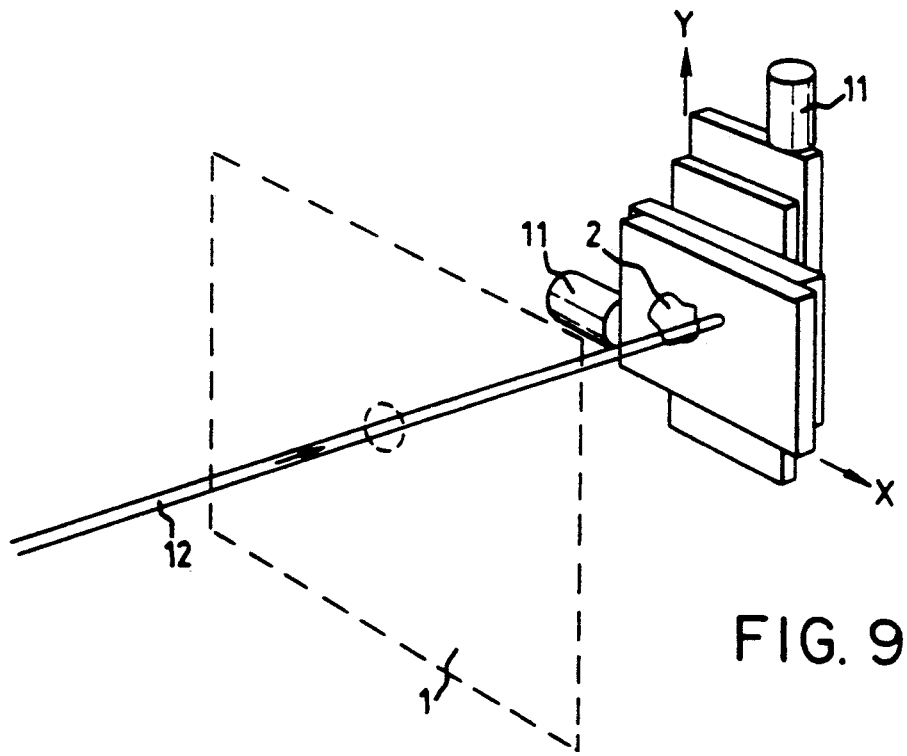
FIG. 9 illustrates a narrow beam method of the invention, in a schematic manner.

FIG. 9 shows an arrangement in which a crystal 2 is translated along X and Y axes in a fixed, narrow X-ray beam. The crystal 2 is mounted on a conventional two-axis slide driven automatically along the X and Y axes by stepping motors 11. A narrow, collimated, fixed X-ray beam 12 is projected, in this case through a central opening in a film or detector 1 so that the back reflection from the crystal 2 is detected.

Figure 10A:
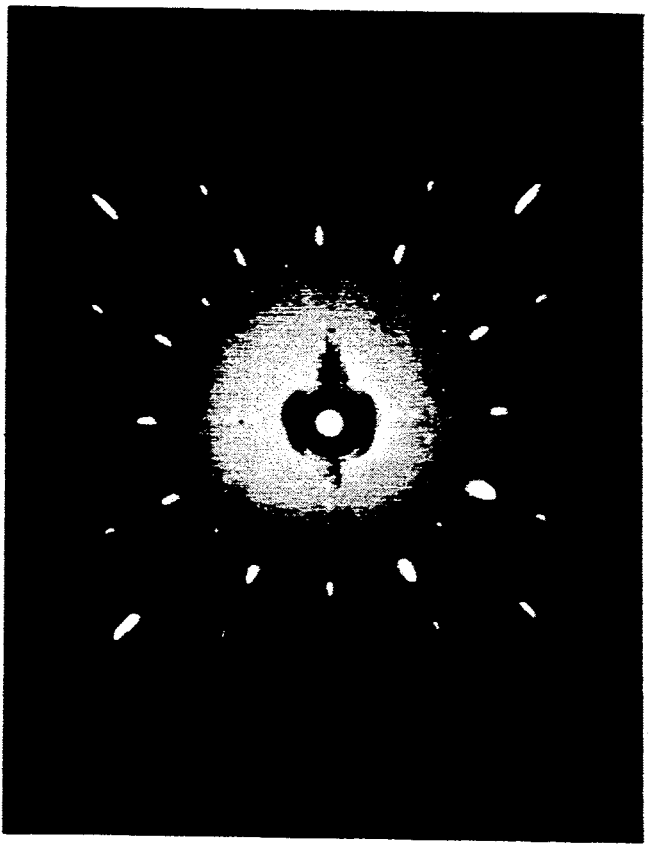
FIGS. 10a and 10b are photographs showing images produced by the method of FIG. 9 from a non-maccled single crystal and a twinned crystal or bicrystal, respectively.
Figure 10B:
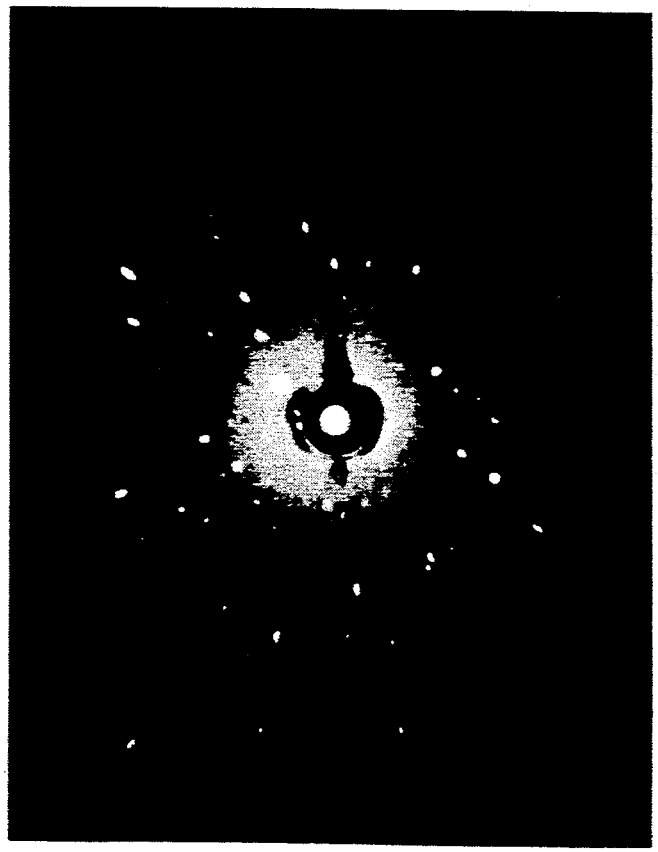

FIGS. 10a and 10b

These photographs were produced using the method of FIG. 9. FIG. 10a has about half the Laue spots of FIG. 10b, indicating that the crystal for FIG. 10a was a single, non-maccled crystal and that the crystal of 10b was a maccle (bicrystal).

FIGS. 11a, 11b and 11c

FIG. 11b shows images produced using the method of FIG. 9; FIG. 11a shows the positions of the beam and its cross-section when the photographs (FIG. 11b) were taken. Each image was photographed onto a different "polaroid" plate (though alternatively a real time detector could have been used). It is not necessary to scan the whole presented profile of the diamond. A and B are the two misorientated volumes-at AB, the two volumes are superimposed. There are three different patterns corresponding to the volumes in the narrow beam, as illustrated in FIG. 11c. As the narrow beam 12 crosses a composition plane, some of the Laue spots fade and others of the Laue spots appear, compare for instance the second and third images from the left in the top row of FIG. 11b.

EXAMPLE 1

Experimental work was done using broad beam X-rays generated by a GEC GX21 rotating-anode generator. This generator has high electron beam current capability of 50 mA at an accelerating voltage of 50 kV with a molybdenum target in "fine focus" mode; the actual experimental work was done using an accelerating voltage of 40 Kv and an electron beam current of 50 mA. In the fine focus mode, the source size was 0.2 mm×1 mm. The generator was fitted with a zirconiun filter to remove Mo KB radiation. The emergent radiation consisted of Bremsstrahlung background, i.e. white or polychromatic X-rays with a continuous wave length distribution, with Mo L and Ka characteristic peaks superimposed. A 1 mm collimator was fitted a distance of 120 mm from the focal spot. The general arrangement was as in FIG. 3.

Laue photographs were taken using a modified "Polaroid" (RTM) film holder which had the collimator removed and bored-out to allow the broad incident X-ray beam to pass through the film. The film holder contained a $Gd_2O_2S$ phosphor in order to reduce exposure time. The camera was placed 0.8 m from the X-ray source so that the incident beam diameter was approximately 8 mm. Photographs were taken using exposure times of 1.0 to 1.5 minutes on "Polaroid" type 57, 3000 ASA high-speed film with a frame size of 127×102 mm (specifically 5×4 inches).

A randomly orientated diamond was mounted on a waxed perspex rod, and a stone-to-film distance of 43 mm was used. The stone was irradiated and the film exposed by back-reflection. Laue spots were counted manually over the whole film frame, and also within a 40 mm radius of the centre of the pattern, i.e. within an angle of 43° to the axis (half angle). The distribution of results was plotted on a graph of number of Laue spots (abscissa) verses frequency (ordinate). In this way, a large number of graphs were produced for various diamonds of different shapes. Stones which had been sorted as non-maccles, but which gave more Laue spots than expected, were examined for misorientated zones (they could be polycrystals or maccles). Stones which had been sorted as maccles, but which gave too few Laue spots, were examined to identify where the technique had failed. It was found that spot counts within a 40 mm radius of the centre (the central 80 mm diameter region) gave slightly better results than counts taken over the whole frame. In general, with a stone-to-film distance of 43 mm, single non-maccled crystals give fewer than 20 spots and maccles, bicrystals or polycrystals gave more than 24 spots. Re-sorting was required for those giving 20 to 24 spots; for instance the orientation could be changed by tilting the perspex rod.

The dividing line between the categories should be that which results in the smallest number of sorting errors. The dividing line was chosen by compiling a table showing the number of sorting errors for various different dividing lines (see the Table below).

There was no need to pre-orientate the sample because the number of Laue spots from each differently oriented zone do not overlap significantly, irrespective of orientation.

The Table below is a table of missorts and was drawn up on the basis of sorting equal numbers of (4Q, 3Q and 2Q mean fourth (poor), third and second quality):
Rounded sawable 4Q maccles
Rounded sawable 4Q non-maccles (single non-maccled crystals)
Thick triangular 2Q chips (single non-maccled crystals)
Thick triangular 3Q chips (single non-maccled crystals)
Thick triangular 2Q maccles
Thick chipped cracked maccles
Thick chipped cracked chips (single non-maccled crystals)
Thin triangular chips (single non-maccled crystals)
Thin triangular maccles
Thin piqueed maccles
Australian chip-type maccles
Australian non-maccles (single non-maccled crystals)
Australian 3Q chips (single non-maccled crystals)
Thick Australian maccles
Sawable Australian maccles
Sawable Australian chips (single non-maccled crystals)
Stepped chips (single non-maccled crystals)
Stepped maccles Bicrystals

TABLE

| Threshold No. of Laue spots | Bicrystals or maccles | % Missorts Average with bi-crystals and maccles | Average without bi-crystals or maccles |
|---|---|---|---|
| 18 | 92 | 33 | 26 |
| 19 | 92 | 27 | 20 |
| 20 | 88 | 21 | 15 |
| 21 | 88 | 17 | 11 |
| 22 | 88 | 17 | 10 |
| 23 | 88 | 19 | 12 |
| 24 | 88 | 21 | 14 |
| 25 | 76 | 23 | 17 |

The "average with bicrystals and maccles" includes the high missort averages for bicrystals, which will be sorted as maccles. In practice, this is not important as the bicrystals can be sorted from the maccles with an automatic shape sort, using for instance the machine disclosed in EP-A-O 227 404.

EXAMPLE 2

The whole volume of a diamond was scanned using a narrow beam; a stepper motor was used to move the stone. The stone was not pre-orientated. Graphs were drawn, based on the photographs, giving the pattern type for the two misorientated volumes A and B, as follows:

A—Strong pattern A
B—Strong pattern B
a—Weak pattern A
b—Weak pattern B and the axes of the graphs represent stepper motor position in the x and y directions.

Maccled stones were distinguished from non-maccled stones by looking for a change in the observed pattern while displacing the stone relative to the beam until the whole volume of the stone had been exposed (see the description of FIGS. 11a to 11c above); this also gives information regarding the position of the misorientated volumes. The first frame of images is used as a reference frame and the later frames are examined for spots in different positions. If the boundary plane is inclined relative to the axis of the X-ray beam, the original spots will weaken and new spots gradually appear as the boundary plane is crossed—in general, the intensity of a Laue spot depends on the thickness of the region giving rise to the spot.

In transmission, the normal zirconium filter in the X-ray generator can be removed to generate more short-wave radiation and reduce Polariod exposure times to 10 seconds.

The present invention had been described above purely by way of example, and modifications can be made within the spirit of the invention. The invention also consists in any individual features described herein or any combination of such features or any generalisation of such features or combination.

I claim:

1. A method of determining the existence of misorientation in a crystal, comprising irradiating the crystal with a beam of substantially parallel incident X-rays without pre-orientating any crystallographic plane of the crystal with respect to the axis of the beam, imaging X-rays received from the crystal so as to cause a plurality of effectively angularly-separated images to be formed, the energy of the X-rays being such that while carrying out the method at least some of the X-rays forming the images have intersected the whole depth of a portion of the crystal being examined, and determining the existence of any misorientation from the images.

2. The method of claim 1, comprising determining which images come from a first volume of the crystal having a first orientation, and which images come from a second volume, if any, of the crystal having a second, different orientation, and thereby determining the existence of misorientation.

3. The method of claim 1, comprising determining the total number of images and comparing this number with a predetermined number representative of a single non-twinned crystal or of a twinned crystal or polycrystal.

4. The method of claim 1, wherein at least one parameter of the images is detected, and peaks in the distribution of the parameter are determined, each peak representing a volume of different orientation.

5. The method of claim 1, wherein the X-rays are imaged adjacent the axis of the incident X-rays, and the existence of any misorientation is determined from those images within a predetermined angle to the axis.

6. The method of claim 1, which is repeated with the crystal in a different orientation relative to the axis of the X-rays.

7. The method of claim 1, wherein shapes of individual spots are compared with projections of the whole cross-section of the crystal.

8. The method of claim 1, wherein it is determined from the images whether there is a spot having a size corresponding to a projected size of the whole cross-section of the stone.

9. The method of claim 1, wherein the X-ray beam is large enough to irradiate the whole crystal simultaneously, and the whole crystal is placed within the beam.

10. The method of claim 1, wherein the X-ray beam is not large enough to irradiate the whole crystal simultaneously.

11. The method of claim 10, wherein the crystal or a portion thereof is irradiated by scanning.

12. The method of claim 11, wherein any change in the pattern of the images as scanning proceeds, is determined.

13. The method of claim 12, in which the position of a second volume of the crystal which has a different orientation from that of the first volume of the crystal, is determined from the location of the scan at which the change occurs.

14. The method of claim 1, wherein said images are formed of X-rays transmitted through the crystal.

15. The method of claim 1, wherein said images are formed of X-rays back-reflected from the crystal.

16. The method of claim 1, wherein a signal is provided indicative of the misorientation in the crystal using automatic image processing and analysis.

17. The method of claim 1, wherein the X-rays are polychromatic.

18. Apparatus for determining the existence of a misorientation in a crystal, comprising:
   means for irradiating the crystal with a beam of substantially parallel X-rays of such an energy that the X-rays penetrate at least half way through a portion of the crystal being examined;
   means for mounting the crystal without pre-orientating any crystallographic plane of the crystal with respect to the axis of the X-rays;
   means for imaging X-rays received from the crystal to thereby form a plurality of effectively angularly-separated images; and
   means for examining said images to thereby determine the existence of any misorientation.

* * * * *

UNITED STATES PATENT AND TRADEMARK OFFICE
CERTIFICATE OF CORRECTION

PATENT NO. : 5,077,767

DATED : December 31, 1991

INVENTOR(S) : Michael P. GAUKROGER

It is certified that error appears in the above-identified patent and that said Letters Patent is hereby corrected as shown below:

On the title page:     column 2, in the Abstract at line 3:

after "X-rays" insert -- without --

Signed and Sealed this

Twenty-seventh Day of April, 1993

*Attest:*

MICHAEL K. KIRK

*Attesting Officer*      Acting Commissioner of Patents and Trademarks